United States Patent
Tang et al.

(10) Patent No.: US 11,538,156 B2
(45) Date of Patent: Dec. 27, 2022

(54) SYSTEM AND METHOD FOR CORONARY CALCIUM DEPOSITS DETECTION AND LABELING

(71) Applicant: TENCENT AMERICA LLC, Palo Alto, CA (US)

(72) Inventors: Hui Tang, Mountain View, CA (US); Tao Yang, Mountain View, CA (US); Yusheng Xie, Mountain View, CA (US); Yaliang Li, Santa Clara, CA (US); Qian Zhen, Palo Alto, CA (US); Wei Fan, New York, NY (US)

(73) Assignee: TENCENT AMERICA LLC, Palo Alto, CA (US)

( * ) Notice: Subject to any disclaimer, the term of this patent is extended or adjusted under 35 U.S.C. 154(b) by 106 days.

(21) Appl. No.: 17/244,564

(22) Filed: Apr. 29, 2021

(65) Prior Publication Data
US 2021/0248743 A1 Aug. 12, 2021

Related U.S. Application Data

(63) Continuation of application No. 16/413,739, filed on May 16, 2019, now Pat. No. 11,030,743.

(51) Int. Cl.
*A61B 5/02* (2006.01)
*G06T 7/00* (2017.01)
(Continued)

(52) U.S. Cl.
CPC ........ *G06T 7/0012* (2013.01); *A61B 5/02007* (2013.01); *A61B 6/503* (2013.01); *G16H 30/40* (2018.01); *A61B 6/032* (2013.01); *G06T 2207/20081* (2013.01); *G06T 2207/20084* (2013.01); *G06T 2207/30048* (2013.01)

(58) Field of Classification Search
None
See application file for complete search history.

(56) References Cited

U.S. PATENT DOCUMENTS

| 2010/0260400 | A1 | 10/2010 | Bernhardt |
| 2011/0144914 | A1* | 6/2011 | Harrington ........ G01N 33/6893 702/19 |

(Continued)

OTHER PUBLICATIONS

Elizabeth R. Brown, ScD et al., "Coronary Calcium Coverage Score: Determination, Correlates, and Predictive Accuracy in the Multi-Ethnic Study of Atherosclerosis 1" Radiology, Jun. 2008, vol. 247, No. 3, pp. 669-678 (11 pages total).

(Continued)

*Primary Examiner* — Idowu O Osifade
(74) *Attorney, Agent, or Firm* — Sughrue Mion, PLLC

(57) ABSTRACT

Embodiments of the present disclosure include a method, device and computer readable medium involving receiving image data of one or more coronary arteries, generating a binary segmentation indicating presence of calcium in the one or more coronary arteries from the image data, generating a branch density of the one or more coronary arteries, and assigning a coronary artery label from the branch density to the binary segmentation such that at least one indication of presence of calcium of the binary segmentation is labeled as present in a specific one of the one or more coronary arteries.

20 Claims, 5 Drawing Sheets

(51) Int. Cl.
*G16H 30/40* (2018.01)
*A61B 6/00* (2006.01)
*A61B 6/03* (2006.01)

(56) References Cited

U.S. PATENT DOCUMENTS

| | | | |
|---|---|---|---|
| 2013/0094749 A1 | 4/2013 | Oh | |
| 2017/0046839 A1 | 2/2017 | Paik et al. | |
| 2017/0337343 A1 | 11/2017 | Kakadiaris | |
| 2019/0138694 A1 | 5/2019 | Tang | |
| 2020/0029923 A1 | 1/2020 | Wilson | |
| 2020/0166523 A1* | 5/2020 | Gill | G01N 33/6872 |
| 2020/0187790 A1 | 6/2020 | Milner | |

OTHER PUBLICATIONS

Guanyu Yang et al., "Automatic coronary calcium scoring using noncontrast and contrast CT images", Medical Physics, May 2016, vol. 43, No. 5, pp. 2174-2186 (13 pages total).
Hui Tang et al., "An Algorithm for Fully Automatic Detection of Calcium in Chest CT Imaging", IEEE, 2017, pp. 265-269 (5 pages total).
International Search Report dated Jul. 20, 2020 from the International Searching Authority in International Application No. PCT/US 20/23251.
Jelmer M. Wolterink et al., "An evaluation of automatic coronary artery calcium scoring methods with cardiac CT using the orCaScore framework", Medical Physics, May 2016, vol. 43, No. 5, pp. 2361-2373 (13 pages total).
Jelmer M. Wolterink et al., "Automatic coronary artery calcium scoring in cardiac CT angiography using paired convolutional neural networks", Elsevier, 2016, pp. 1-14 (14 pages total).
Jelmer M. Wolterink et al., "Automatic Coronary Calcium Scoring in Cardiac CT Angiography Using Convolutional Neural Networks", Springer International Publishing Switzerland, 2015, Part 1, LNCS 9349, pp. 589-596 (8 pages total).
Olaf Ronneberger et al., "U-Net: Convolutional Networks for Biomedical Image Segmentation", Springer International Publishing Switzerland, 2015, Part III, LNCS 9351, pp. 234-241 (8 pages total).
Rahil Shahzad, MSc et al., "Vessel Specific Coronary Artery Calcium Scoring: An Automatic System", Academic Radiology, Jan. 2013, vol. 20, No. 1, pp. 1-9 (10 pages total).
Ran Shadmi et al., "Fully-Convolutional Deep-Learning Based System for Coronary Calcium Score Prediction from Non-Contrast Chest CT", IEEE, Apr. 4-7, 2018, 15th International Symposium on Biomedical Imaging, pp. 24-28 (5 pages total).
Robert Detrano, M.D., Ph.D. et al., "Coronary Calcium as a Predictor of Coronary Events in Four Racial or Ethnic Groups", New England Journal of Medicine, Mar. 27, 2008, vol. 358, No. 13, pp. 1336-1345 (11 pages total).
Tamar S. Polonsky, MD, et al., "Coronary Artery Calcium Score and Risk Classification for Coronary Heart Disease Prediction: The Multi-Ethnic Study of Atherosclerosis", The Journal of the American Medical Association, Apr. 28, 2010, vol. 303, No. 16, pp. 1-14 (15 pages total).
Written Opinion dated Jul. 20, 2020 from the International Bureau in International Application No. PCT/US 20/23251.
Zhen Qian, PhD et al., "Lesion- and vessel-specific coronary artery calcium scores are superior to whole-heart Agatston and volume scores in the diagnosis of obstructive coronary artery disease", Journal of Cardiovascular Computed Tomography, Nov./Dec. 2010, vol. 4, No. 6, pp. 391-399 (9 pages total).

* cited by examiner

SYSTEM AND METHOD FOR CORONARY CALCIUM DEPOSITS DETECTION AND LABELING

CROSS-REFERENCE TO RELATED APPLICATION

This application is a continuation of U.S. application Ser. No. 16/413,739, filed May 16, 2019, the contents of which are incorporated herein by reference.

BACKGROUND

Coronary artery calcium (CAC) is an independent predictor of future coronary events. The conventional CAC quantification software assesses the coronary calcium burden on a whole-heart basis. However, a three-dimensional (3D) CAC volume may contain unused important additional information, such as the number of the involved coronary arteries and the calcium burden of each artery, that is left unused, such as by prevailing whole-heart metrics like Agatston scores and volume scores. Various background non-patent literature (NPL) are listed below and involve such problems.

With NPL 1 and NPL 2, CAC may be used as an independent predictor of future coronary events.

With NPL 3, a percentage of the coronary arteries afflicted by calcium may be a better predictor of coronary risk than an Agatston score.

With NPL 4, a vessel-specific calcium score for individual vessels may be a better predictor of obstructive diseases rather than a whole-heart calcium score.

With NPL 5-11, algorithms have attempted for automatic calcium deposit detection in a CT context. With NPL 5-7, traditional machine learning based methods have been attempted, and with NPl 8-11, relatively more recent deep learning based methods have been attempted.

However, disadvantageously, such attempts with traditional machine learning require feature engineering and are therefore time consuming. For example, with traditional machine learning based methods of NPL 5-7, a threshold at a fixed Hounsfield Unit is used to get candidate objects for classification. Different features, such as first order and second order intensity features at different scales as well as shape and location features of each spot are extracted, which turns to be a substantially, and possibly most, time-consuming step since this step has been needed for both the training stage and the testing stage.

With NPL 8 and 9, there has been first performed a threshold to get a set of candidate objects of calcified lesions. For each object, convoluted neural network (CNN) features from the axial, coronary and sagittal planes centered at the object's center, together with hand crafted position features were calculated and fed to a random forest classifier.

With NPL 10 and 12, there has been direct learning of a binary mask from a calcium segmentation mask using a 2D UNET. Such a mask has turned out to perform poorly in detecting coronary calcium. Even with further thresholding an original raw image with a fixed Hounsfield Unit and multiplying the mask from the thresholding with the mask from the 2D UNet, these deep learning based methods were not able to assign a coronary artery branch to each of detected calcium lesions.

NPL 1: Detrano R, Guerci A D, Carr J J, Bild D E, Burke G, Folsom A R, Liu K, Shea S, Szklo M, Bluemke D A, O'leary D H. *Coronary calcium as a predictor of coronary events in four racial or ethnic groups*. New England Journal of Medicine. 2008 Mar. 27; 358(13):1336-45.

NPL 2: Polonsky T S, McClelland R L, Jorgensen N W, Bild D E, Burke G L, Guerci A D, Greenland P. *Coronary artery calcium score and risk classification for coronary heart disease prediction*. Jama. 2010 Apr. 28; 303(16): 1610-6.

NPL 3: Brown E R, Kronmal R A, Bluemke D A, et al. *Coronary calcium coverage score: determination, correlates, and predictive accuracy in the Multi-Ethnic Study of Atherosclerosis*. Radiology 2008; 247:669-75.

NPL 4: Qian Z, Anderson H, Marvasty I, et al. *Lesion-and vessel-specific coronary artery calcium scores are superior to whole-heart Agatston and volume scores in the diagnosis of obstructive coronary artery disease*. J Cardiovasc Comput Tomogr 2010; 4:391-399.

NPL 5: Wolterink J M, Leiner T, De Vos B D, Coatrieux J L, Kelm B M, Kondo S, Salgado R A, Shahzad R, Shu H, Snoeren M, Takx R A. *An evaluation of automatic coronary artery calcium scoring methods with cardiac CT using the orCaScore framework*. Medical physics. 2016 May 1; 43(5):2361-73.

NPL 6: Yang G, Chen Y, Ning X, Sun Q, Shu H, Coatrieux J L. *Automatic coronary calcium scoring using noncontrast and contrast CT images*. Medical physics. 2016 May 1; 43(5):2174-86.

NPL 7: Shahzad R, van Walsum T, Schaap M, Rossi A, Klein S, Weustink A C, de Feyter P J, van Vliet L J, Niessen W J. *Vessel specific coronary artery calcium scoring: an automatic system*. Academic radiology. 2013 Jan. 1; 20(1):1-9.

NPL 8: Tang H, Moradi M, Prasanna P, Wang H, Syeda-Mahmood T. *An algorithm for fully automatic detection of calcium in chest ct imaging*. In Biomedical Imaging (ISBI 2017), 2017 IEEE 14th International Symposium on 2017 Apr. 18 (pp. 265-269). IEEE NPL 9: Wolterink J M, Leiner T, Viergever M A, Išgum I. *Automatic coronary calcium scoring in cardiac CT angiography using convolutional neural networks*. In International Conference on Medical Image Computing and Computer-Assisted Intervention 2015 Oct. 5 (pp. 589-596). Springer, Cham.

NPL 10: Wolterink J M, Leiner T, de Vos B D, van Hamersvelt R W, Viergever M A, Išgum I. *Automatic coronary artery calcium scoring in cardiac CT angiography using paired convolutional neural networks*. Medical image analysis. 2016 Dec. 1; 34:123-36.

NPL 11: Shadmi R, Mazo V, Bregman-Amitai O, Elnekave E. *Fully-convolutional deep-learning based system for coronary calcium score prediction from non-contrast chest CT*. In Biomedical Imaging (ISBI 2018), 2018 IEEE 15th International Symposium on 2018 Apr. 4 (pp. 24-28). IEEE.

NPL 2: Ronneberger O, Fischer P, Brox T. U-net: *Convolutional networks for biomedical image segmentation*. In International Conference on Medical image computing and computer-assisted intervention 2015 Oct. 5 (pp. 234-241). Springer, Cham.

SUMMARY

Automatic detection of CAC lesions and labeling of corresponding arterial territories are prerequisite for automation of comprehensive analysis for a CAC study. Herein is disclosed a system that automatically detects coronary deposits and provides coronary artery territorial labeling to each calcium lesion. Embodiments may include two models.

One of those models is disclosed herein as a binary segmentation model that segments calcium deposits in a medical image, such as a computed tomography CT image. Embodiments may segment all calcium deposits in such medical image. Such model may be a segmentation network that tells, for each voxel in a CT image, whether the voxel belongs to a calcium deposit.

Another of those models is disclosed herein as an encoder-decoder model that learns density of each coronary artery branch. Such model tells, for each voxel in a CT image, which coronary artery territory the voxel belongs to and to what probability the voxel belongs to that coronary artery territory. Embodiments may determine the coronary artery territory label of each calcium lesion by averaging a branch density inside each spot.

Herein is disclosed deep learning bases and thus do not need to extract any hand-crafted features. Herein is disclosed a system learning two encoder-decoder models to map an original image to two types of outputs, one of which learns a binary calcium segmentation mask, and another of which learns the coronary artery branch density. Combining the two models yields an ability to tell a coronary artery branch for each calcium spot.

Such embodiments may be used in annual physical checking's together with other clinical findings to stratify a subject's risk of cardiac events without disadvantages of the above-described NPL.

For example, here is disclose a deep learning-based model in which a feature extraction step can be eliminated. If run on graphics processing units (GPU), the whole process of testing takes a few milliseconds according to embodiments. Deep learning-based algorithms are more time efficient; however, prior, even recently proposed, deep learning based methods are able to tell a coronary artery branch label for each calcium lesion. Accordingly, embodiments learn a coronary branch density distribution from a deep learning model and combine it with a binary calcium deposits detection model to label calcium lesions.

The disclosure herein solves various problems. For example, the disclosure represents more time efficiency than tradition machine learning based algorithms, and the disclosure represents a novel ability to automatically assign a coronary branch label to one or more calcium lesions, in contrast to other deep learning based coronary calcium detection methods which are not able to assign a coronary branch label to one or more calcium lesions.

Additionally, the components described herein may respectively comprise at least one memory configured to store computer program code, and at least one processor, such as a hardware processor, configured to access the at least one memory and operate according to the computer program code, where the computer program code comprises various codes, described as units throughout according to embodiments, configured to cause the at least one processor to implement various features.

According to some possible implementations, there is a method implemented by one or more processors, a memory, and one or more programs, the one or more programs being stored in the memory, the program comprising one or more modules each corresponding to a set of instructions, the one or more processors being configured to execute the instructions, and the method comprising receiving image data of one or more coronary arteries, generating a binary segmentation indicating presence of calcium in the one or more coronary arteries from the image data, generating a branch density of the one or more coronary arteries, and assigning a coronary artery label from the branch density to the binary segmentation such that at least one indication of presence of calcium of the binary segmentation is labeled as present in a specific one of the one or more coronary arteries.

According to some possible implementations, the method may include generating the binary segmentation by a first neural network, and generating the branch density is implemented by a second neural network.

According to some possible implementations, the method may include training the first neural network, and training the second neural network.

According to some possible implementations, the method may include training the first neural network by generating a binary calcium segmentation mask from training data.

According to some possible implementations, the method may include training the second neural network by annotating one or more training branches of a training data coronary artery and estimating ground truth density of the one or more training branches.

According to some possible implementations, the method may include training the second neural network by annotating four major branches of the training data coronary artery, and the four major branches comprise a left main artery, a left anterior descending artery, a left circumflex artery, and a right coronary artery.

According to some possible implementations, the method may include training the second neural network by annotating other branches of the training data coronary artery in addition to the four major branches.

According to some possible implementations, the method may include a first loss defined in training the first neural network as different than a second loss defined in training the second neural network According to some possible implementations, the method may include assigning the coronary artery label by averaging a plurality of labels from a plurality of detected spots of calcium.

According to some possible implementations, the method may include generating the binary segmentation and generating the branch density by a first neural network.

According to some possible implementations, there is an apparatus comprising at least one memory configured to store computer program code, and at least one processor configured to access the at least one memory and operate according to the computer program code.

The computer program code comprising receiving code configured to cause the at least one processor to receive image data of one or more coronary arteries, generating code configured to cause the at least one processor to generate a binary segmentation indicating presence of calcium in the one or more coronary arteries from the image data, generating code configured to cause the at least one processor to generate a branch density of the one or more coronary arteries, and assigning code configured to cause the at least one processor to assign a coronary artery label from the branch density to the binary segmentation such that at least one indication of presence of calcium of the binary segmentation is labeled as present in a specific one of the one or more coronary arteries.

According to some possible implementations, there is a non-transitory computer-readable medium storing instructions. The instructions comprising one or more instructions that, when executed by one or more processors of a device, cause the one or more processors to receive image data of one or more coronary arteries, generate a binary segmentation indicating presence of calcium in the one or more coronary arteries from the image data, generate a branch density of the one or more coronary arteries, and assign a coronary artery label from the branch density to the binary segmentation such that at least one indication of presence of calcium of the binary segmentation is labeled as present in a specific one of the one or more coronary arteries.

DETAILED DESCRIPTION

Figure 1:
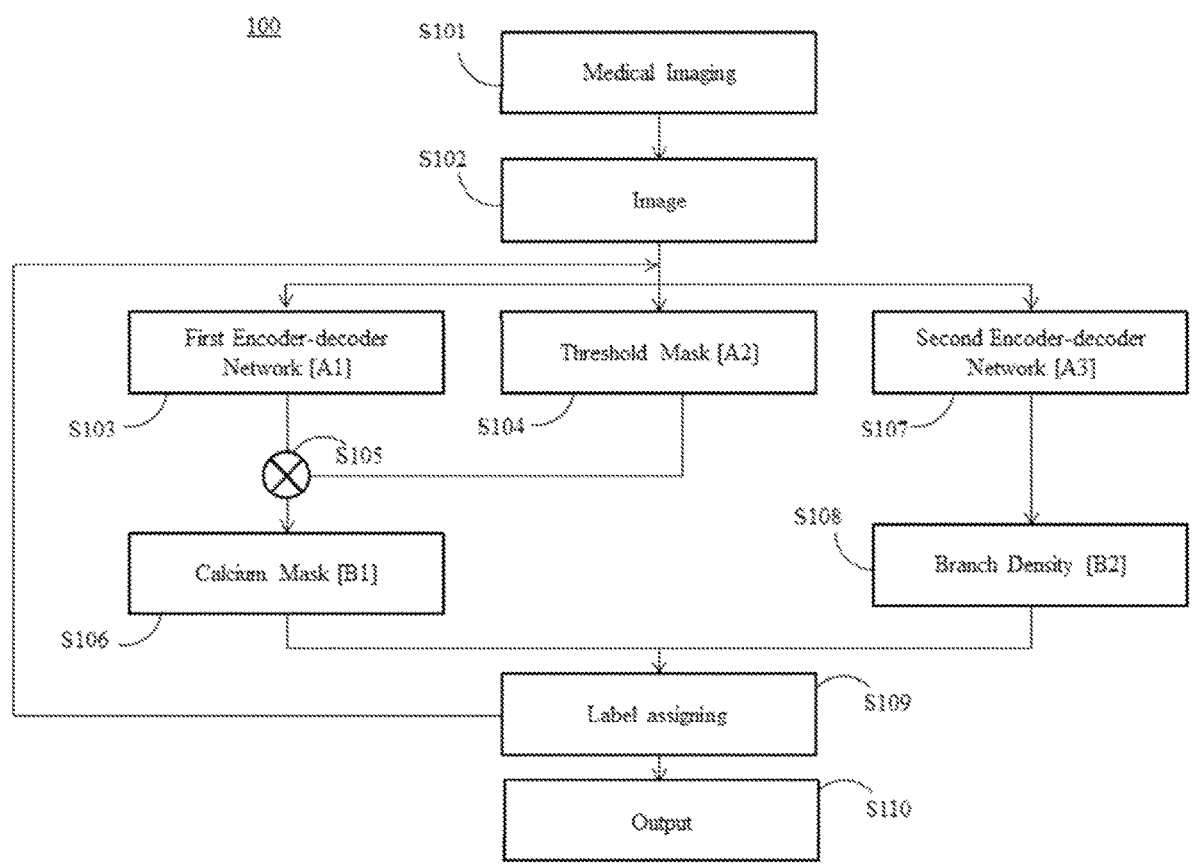
FIG. 1 is a flowchart 100 according to embodiments of the present disclosure.

FIG. 1 shows a flowchart 100 according to embodiments of the present disclosure. Advantageously, the flowchart 100 illustrates an ability to automatically determine a detected calcium lesion's coronary arterial territory, that is, an ability to determine which coronary artery branch, for example, in which a calcium lesion resides.

At S101, medical imaging occurs, such as x-ray, to obtain data regarding, for example, part of or an entirety of a coronary circuit of a patient. Other imaging modalities are applicable in that calcium may be detected therein the patient.

At S102, an image, such as a raw image, from the medical imaging is fed into two encoder-decoder networks, such as the first encoder-decoder network indicated in S103 and the second encoder-decoder network indicated in S107. The networks may be considered neural networks of which an untrained neural network model, through deep learning framework described below in conjunction with a training data set, may result in a trained data set by which testing with input data may result in optimized use of the neural network in a testing environment. Training stages for these networks are described further below with the other figures, such as FIG. 2 and FIG. 3.

Figure 2:
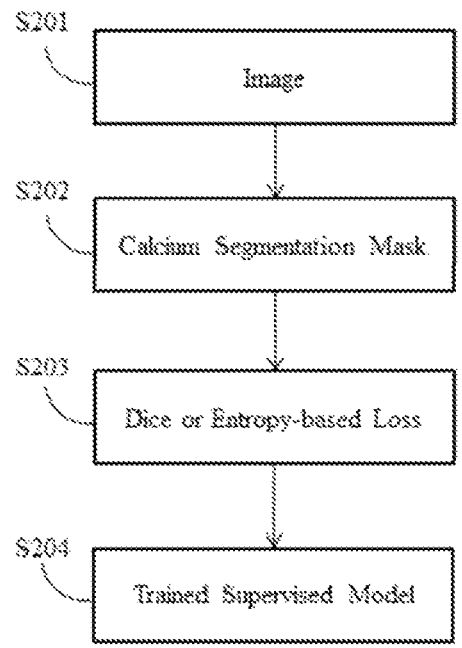
FIG. 2 is a flowchart 100 according to embodiments of the present disclosure.

During the testing stage, at S105, a threshold mask obtained at S104 is multiplied with an output of the first encoder-decoder network's consideration, as compared with the training involved in FIG. 2, at S103 of the input image from S102.

An output of the testing stage at S105 may be viewed as a calcium segmentation mask, such as a value 1 indicating calcium and 0 indicating a background from the input image. As such, an output of S105, may at S106 be a binary segmentation of calcium.

Further during the testing stage, the image from S102 may also be, in parallel or in sequence with the first encoder-decoder network, be input to the second encoder-decoder network at S107, and a result of the second encoder-decoder networks consideration of the image from S102 may be output as a coronary artery density, a branch density, as indicated in S108.

Thereby during the testing stage, the calcium segmentation from S106 and the branch density from S108 may be combined into the label assigning of S109. That is, for each pixel in each detected calcium lesion, such as in the testing stage output S106 of the first encoder-decoder network, may be automatically assigned to a coronary artery density label by looking at the coronary artery density image, such as from the testing stage output S108 of the second encoder-decoder network. An overall label of each calcium lesion is defined by, for example, averaging, in S109, a label inside each calcium spot. The process of flowchart 100 may be reiterated if further data remains unanalyzed, and one or more outputs S110 may be output. Such output may be to a graphical user interface as described below with FIG. 4 wherein a user, such as a technician, may review a result of the automatically detected calcium lesion's coronary arterial territory.

FIG. 2 illustrates a flowchart 200 regarding training a first encoder-decoder network. At S201, an image, such as a medical image regarding one or more coronary artery scans which may be training data, is fed into training a first encoder decoder network, such as employed in FIG. 1 S103 according to exemplary embodiments. Elements with this FIG. 2 may be considered training data according to exemplary embodiments. At S202, a calcium segmentation mask, such as a value 1 indicating calcium and a value 0 indicating background, may be set, with respect to the image from S201, as a ground truth for training, for example for hypothesis testing purposes. Further training of the first encoder-decoder network, since outputs from S202 may be either the above-noted value 1 or value 0, embodiments employ any of dice-based or cross-entropy based loss at S203, for example with respect to considerations of class imbalance and backpropagation. From there, the flowchart 200 may be reiterated to further train the first encoder-decoder network or may be output at S204 as a trained supervised model for use in S103 of the flowchart 100 of FIG. 1.

Figure 3:
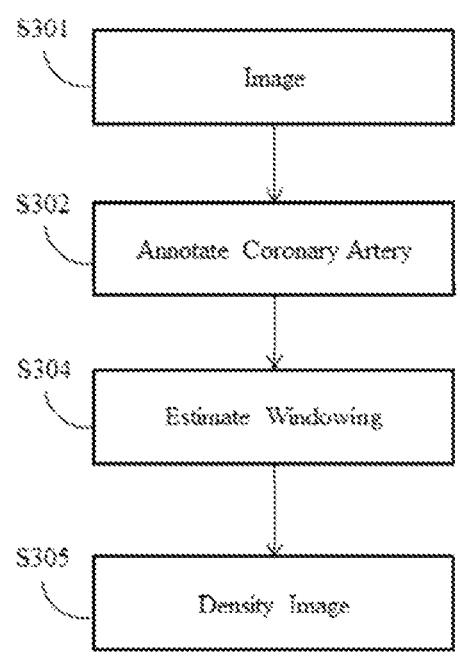
FIG. 3 is a flowchart 100 according to embodiments of the present disclosure.

FIG. 3 illustrates a flowchart 300 regarding training, such as generating ground truth of a coronary artery density map, a second encoder-decoder network, and may be performed in parallel or in sequence with the flowchart 200 of FIG. 2. Elements with this FIG. 3 may be considered training data according to exemplary embodiments. At S301, an image, such as a medical image regarding one or more coronary artery scans, which may be training data, is fed into training a second encoder decoder network, such as employed in FIG. 1. S107 according to exemplary embodiments. With respect to the input image of S301, at S302, branches of the coronary artery, such as four major branches: left main artery (LM), left anterior descending artery (LAD), left circumflex artery (LCX), and right coronary artery (RCA), may be annotated from, for example, a coronary computer tomography angiography (CTA) with respect to the input image of S301. Thereafter, at S304, ground truth density may be estimated with respect to various windowing, such as Parzen windowing, kernel density estimation, to result in a density image at S304 having an intensity between 0 and 1, for example. From there, the flowchart 300 may be reiterated to further train the second encoder-decoder network or may be output as a trained supervised model for use in S107 of the flowchart 100 of FIG. 1. According to exemplary embodiments, the second encoder-decoder network may have a same architecture as a first encoder-decoder network, but, in various embodiments, a loss used with the second encoder-decoder network training may be different as compared to training the first encoder-decoder network. According to exemplary embodiments, a mean squared error may be used as a loss in optimizing training stages.

Alternatively, more branches of coronary arteries, rather than four major branches, could also be learned, labeled, and output in addition or instead of the other herein described embodiments.

The techniques disclosed herein, can be implemented as computer software using computer-readable instructions and physically stored in one or more computer-readable media. For example, FIG. 4 shows a computer system 400 suitable for implementing certain embodiments of the disclosed subject matter.

The computer software can be coded using any suitable machine code or computer language, that may be subject to assembly, compilation, linking, or like mechanisms to create code comprising instructions that can be executed directly, or through interpretation, micro-code execution, and the like, by computer central processing units (CPUs), Graphics Processing Units (GPUs), and the like.

The instructions can be executed on various types of computers or components thereof, including, for example, personal computers, tablet computers, servers, smartphones, gaming devices, internet of things devices, and the like.

Figure 4:
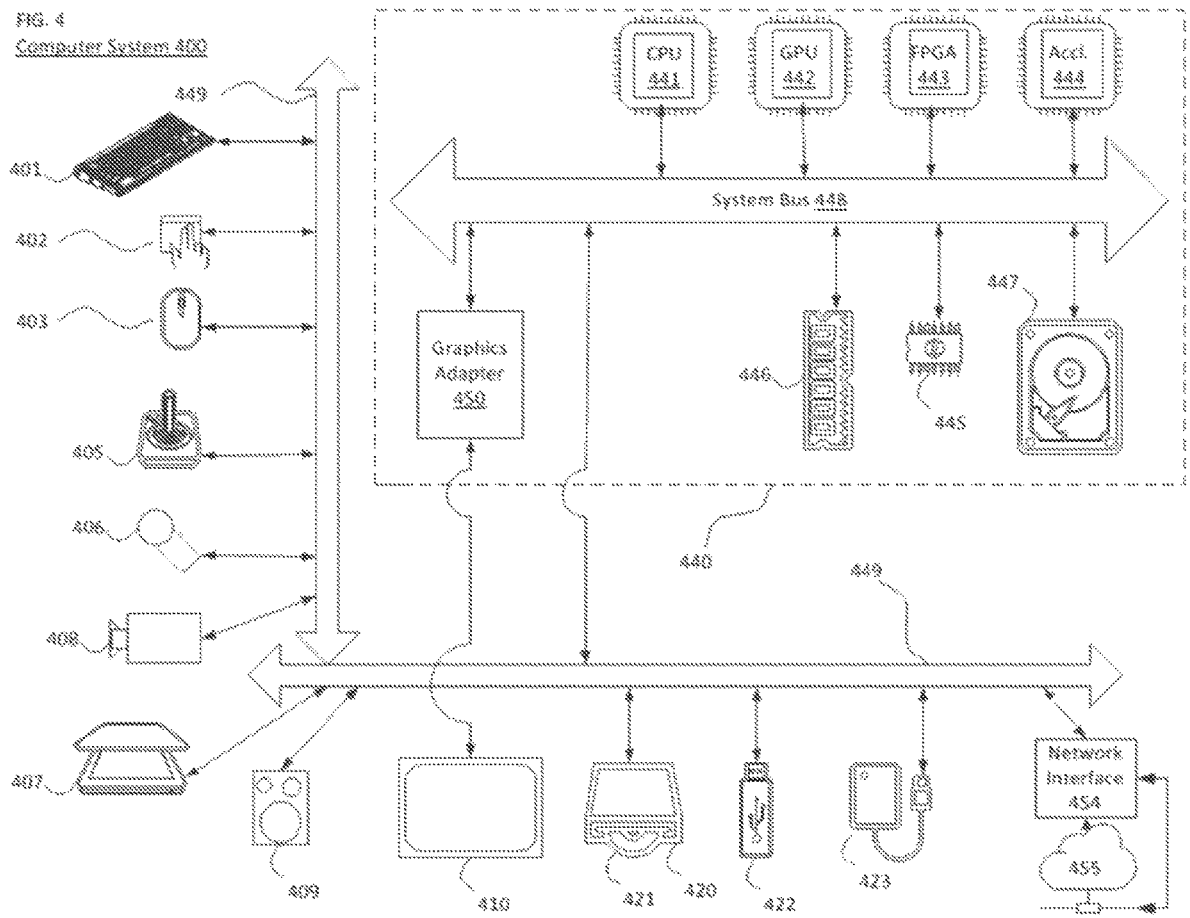
FIG. 4 is an illustration 400 of various components according to embodiments of the present disclosure.

The components shown in FIG. 4 for computer system 400 are exemplary in nature and are not intended to suggest any limitation as to the scope of use or functionality of the computer software implementing embodiments of the present disclosure. Neither should the configuration of components be interpreted as having any dependency or requirement relating to any one or combination of components illustrated in the exemplary embodiment of a computer system 400.

Computer system 400 may include certain human interface input devices. Such a human interface input device may be responsive to input by one or more human users through, for example, tactile input (such as: keystrokes, swipes, data glove movements), audio input (such as: voice, clapping), visual input (such as: gestures), olfactory input (not depicted). The human interface devices can also be used to capture certain media not necessarily directly related to conscious input by a human, such as audio (such as: speech, music, ambient sound), images (such as: scanned images, photographic images obtain from a still image camera), video (such as two-dimensional video, three-dimensional video including stereoscopic video).

Input human interface devices may include one or more of (only one of each depicted): keyboard 401, mouse 402, trackpad 403, touch screen 410, joystick 405, microphone 406, scanner 407, and camera 408. The camera 408 may be x-ray equipment, or other medical technology, for cardiac computed tomography from which the image of S101 or S501 may be obtained for example.

Computer system 400 may also include certain human interface output devices. Such human interface output devices may be stimulating the senses of one or more human users through, for example, tactile output, sound, light, and smell/taste. Such human interface output devices may include tactile output devices (for example tactile feedback by the touch-screen 410, or joystick 405, but there can also be tactile feedback devices that do not serve as input devices), audio output devices (such as: speakers 409, headphones (not depicted)), visual output devices (such as screens 410 to include CRT screens, LCD screens, plasma screens, OLED screens, each with or without touch-screen input capability, each with or without tactile feedback capability—some of which may be capable to output two dimensional visual output or more than three dimensional output through means such as stereographic output; virtual-reality glasses (not depicted), holographic displays and smoke tanks (not depicted)), and printers (not depicted).

Computer system 400 can also include human accessible storage devices and their associated media such as optical media including CD/DVD ROM/RW 420 with CD/DVD or the like media 421, thumb-drive 422, removable hard drive or solid state drive 423, legacy magnetic media such as tape and floppy disc (not depicted), specialized ROM/ASIC/PLD based devices such as security dongles (not depicted), and the like.

Those skilled in the art should also understand that term "computer readable media" as used in connection with the presently disclosed subject matter does not encompass transmission media, carrier waves, or other transitory signals.

Computer system 400 can also include interface to one or more communication networks. Networks can for example be wireless, wireline, optical. Networks can further be local, wide-area, metropolitan, vehicular and industrial, real-time, delay-tolerant, and so on. Examples of networks include local area networks such as Ethernet, wireless LANs, cellular networks to include GSM, 3G, 4G, 5G, LTE and the like, TV wireline or wireless wide area digital networks to include cable TV, satellite TV, and terrestrial broadcast TV, vehicular and industrial to include CANBus, and so forth. Certain networks commonly require external network interface adapters that attached to certain general-purpose data ports or peripheral buses (449) (such as, for example USB ports of the computer system 400; others are commonly integrated into the core of the computer system 400 by attachment to a system bus as described below (for example Ethernet interface into a PC computer system or cellular network interface into a smartphone computer system). Using any of these networks, computer system 400 can communicate with other entities. Such communication can be uni-directional, receive only (for example, broadcast TV), uni-directional send-only (for example CANbusto certain CANbus devices), or bi-directional, for example to other computer systems using local or wide area digital networks. Certain protocols and protocol stacks can be used on each of those networks and network interfaces as described above.

Aforementioned human interface devices, human-accessible storage devices, and network interfaces can be attached to a core 440 of the computer system 400.

The core 440 can include one or more Central Processing Units (CPU) 441, Graphics Processing Units (GPU) 442, specialized programmable processing units in the form of Field Programmable Gate Areas (FPGA) 443, hardware accelerators for certain tasks 444, and so forth. These devices, along with Read-only memory (ROM) 145, Random-access memory 446, internal mass storage such as internal non-user accessible hard drives, SSDs, and the like 447, may be connected through a system bus 448. In some computer systems, the system bus 448 can be accessible in the form of one or more physical plugs to enable extensions by additional CPUs, GPU, and the like. The peripheral devices can be attached either directly to the core's system bus 448, or through a peripheral bus 449. Architectures for a peripheral bus include PCI, USB, and the like.

CPUs 441, GPUs 442, FPGAs 443, and accelerators 444 can execute certain instructions that, in combination, can make up the aforementioned computer code. That computer code can be stored in ROM 445 or RAM 446. Transitional data can also be stored in RAM 446, whereas permanent data can be stored for example, in the internal mass storage 447. Fast storage and retrieve to any of the memory devices can be enabled through the use of cache memory, that can be closely associated with one or more CPU 441, GPU 442, mass storage 447, ROM 445, RAM 446, and the like.

The computer readable media can have computer code thereon for performing various computer-implemented operations. The media and computer code can be those specially designed and constructed for the purposes of the present disclosure, or they can be of the kind well known and available to those having skill in the computer software arts.

As an example and not by way of limitation, the computer system having architecture 400, and specifically the core 440 can provide functionality as a result of processor(s) (including CPUs, GPUs, FPGA, accelerators, and the like) executing software embodied in one or more tangible, computer-readable media. Such computer-readable media can be media associated with user-accessible mass storage as introduced above, as well as certain storage of the core 440 that are of non-transitory nature, such as core-internal mass storage 447 or ROM 445. The software implementing various embodiments of the present disclosure can be stored in such devices and executed by core 440. A computer-readable medium can include one or more memory devices or chips, according to particular needs. The software can cause the core 740 and specifically the processors therein (including CPU, GPU, FPGA, and the like) to execute particular processes or particular parts of particular processes described herein, including defining data structures stored in RAM 446 and modifying such data structures according to the processes defined by the software. In addition or as an alternative, the computer system can provide functionality as a result of logic hardwired or otherwise embodied in a circuit (for example: accelerator 444), which can operate in place of or together with software to execute particular processes or particular parts of particular processes described herein. Reference to software can encompass logic, and vice versa, where appropriate. Reference to a computer-readable media can encompass a circuit (such as an integrated circuit (IC)) storing software for execution, a circuit embodying logic for execution, or both, where appropriate. The present disclosure encompasses any suitable combination of hardware and software.

Figure 5:
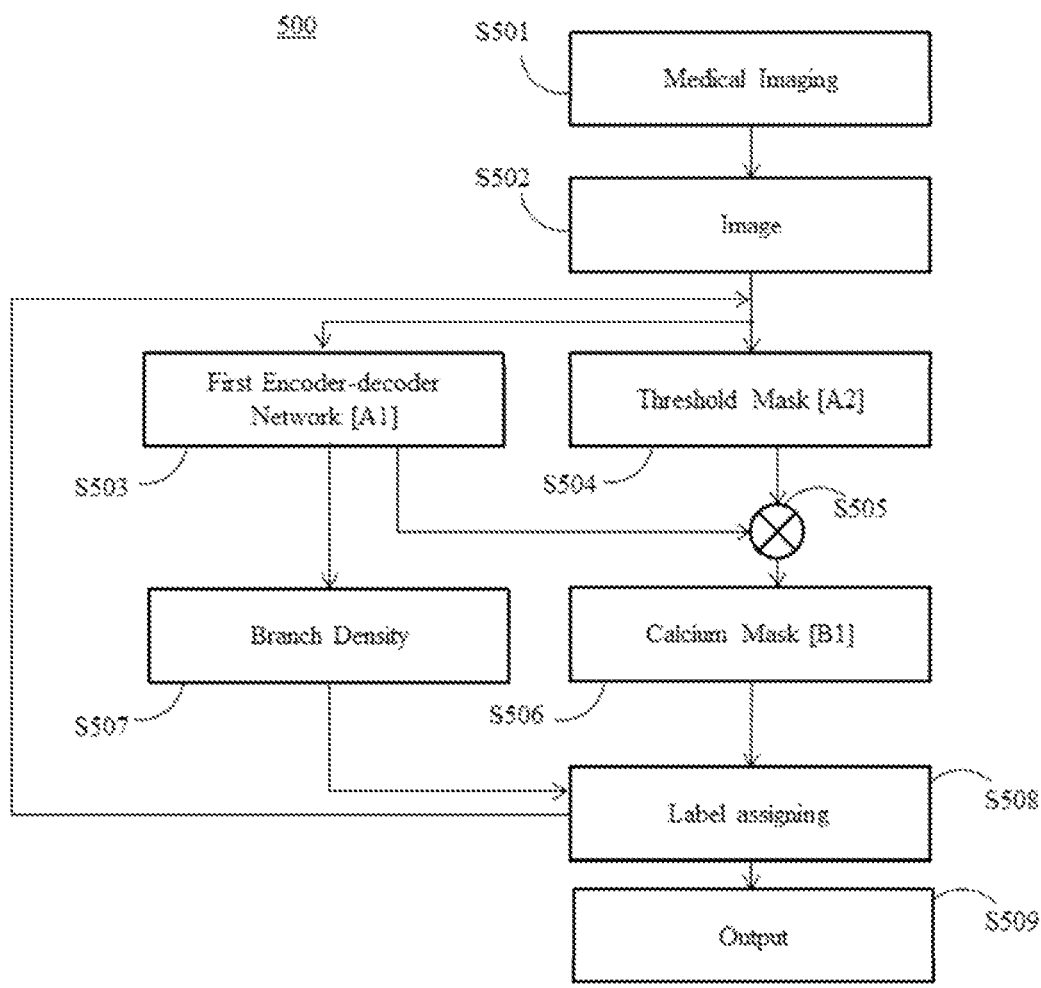
FIG. 5 is a flowchart 100 according to embodiments of the present application.

FIG. 5 shows a flowchart 500 according to embodiments of the present disclosure. Advantageously, the flowchart 500 illustrates an ability to automatically determine a detected calcium lesion's coronary arterial territory according to embodiments. Instead of learning the coronary artery branch density separately, a label of the coronary artery branch can be learned directly from a first encoder-decoder model which performs a multi-label output instead of a binary output, but, according to embodiments, since the calcium spots may be sparsely distributed in CT images, such embodiments may be over-trained.

At S501, medical imaging occurs, such as x-ray, to obtain data regarding, for example, part of or an entirety of a coronary circuit of a patient. Other imaging modalities are applicable in that calcium may be detected therein the patient.

At S502, an image, such as a raw image, from the medical imaging is fed into an encoder-decoder network, such as the first encoder-decoder network indicated in S503. Training stages for hat networks are described above as a combination with figures, such as FIG. 2 and FIG. 3.

During the testing stage, at S505, a threshold mask obtained at S504 is multiplied with an output of the first encoder-decoder network's consideration, as compared with the training involved in FIG. 2, at S503 of the input image from S502.

An output of the testing stage at S505 may be viewed as a calcium segmentation mask, such as a value 1 indicating calcium and 0 indicating a background from the input image. As such, an output of S505, may at S506 be a binary segmentation of calcium from the input image.

Further during the testing stage, the image from S502 may also be, in parallel or in sequence with the first encoder-decoder network at S503 a result in consideration of the image from S102 to be output as a coronary artery density, a branch density, as indicated in S507.

Thereby during the testing stage, the calcium segmentation from S506 and the branch density from S507 may be combined into the label assigning of S508. That is, for each pixel in each detected calcium lesion, such as in the testing stage output S506 of the first encoder-decoder network, may be automatically assigned to a coronary artery density label by looking at the coronary artery density image, such as from the testing stage output S508 of the first encoder-decoder network. An overall label of each calcium lesion is defined by, for example, averaging, in S508, a label inside each calcium spot. The process of flowchart 500 may be reiterated if further data remains unanalyzed, and one or more outputs S509 may be output. Such output may be to a graphical user interface as described above with FIG. 4 wherein a user, such as a technician, may review a result of the automatically detected calcium lesion's coronary arterial territory.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, or a combination of hardware and software.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware may be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A method implemented by one or more processors, a memory, and one or more programs, the one or more programs being stored in the memory, the program comprising one or more modules each corresponding to a set of instructions, the one or more processors being configured to execute the instructions, and the method comprising:
receiving image data;
generating data indicating presence of calcium in one or more coronary arteries from the image data;
generating, in parallel with generating the data, a branch density of the one or more coronary arteries; and
assigning a coronary artery label from the branch density to a specific one of the one or more coronary arteries.

2. The method of claim 1,
wherein generating the data is implemented by a first neural network, and
wherein generating the branch density is implemented by a second neural network.

3. The method of claim 2, further comprising:
training the first neural network; and
training the second neural network.

4. The method of claim 3, wherein training the first neural network comprises generating a binary calcium segmentation mask from training data.

5. The method of claim 3, wherein training the second neural network comprises annotating one or more training branches of a training data coronary artery and estimating ground truth density of the one or more training branches.

6. The method of claim 5, wherein training the second neural network further comprises annotating four major branches of the training data coronary artery, and
wherein the four major branches comprise a left main artery, a left anterior descending artery, a left circumflex artery, and a right coronary artery.

7. The method of claim 6, wherein training the second neural network comprises annotating other branches of the training data coronary artery in addition to the four major branches.

8. The method of claim 3, wherein a first loss defined in training the first neural network is different than a second loss defined in training the second neural network.

9. The method of claim 1, wherein assigning the coronary artery label comprises averaging a plurality of labels from a plurality of detected spots of calcium.

10. The method of claim 1, wherein generating the data and generating the branch density are implemented by a first neural network.

11. An apparatus comprising:
at least one memory configured to store computer program code; and
at least one processor configured to access the at least one memory and operate according to the computer program code, the computer program code comprising:
receiving code configured to cause the at least one processor to receive image data;
first generating code configured to cause the at least one processor to generate a data indicating presence of calcium in one or more coronary arteries from the image data;
second generating code configured to cause the at least one processor to generate, in parallel with generating the data, a branch density of the one or more coronary arteries; and
assigning code configured to cause the at least one processor to assign a coronary artery label from the branch density to a specific one of the one or more coronary arteries.

12. The apparatus of claim 11,
wherein generating the data is implemented by a first neural network of the at least one processor, and
wherein generating the branch density is implemented by a second neural network of the at least one processor.

13. The apparatus of claim 12, wherein the computer code further comprises:
first training code configured to cause the at least one processor to train the first neural network; and
second training code configured to cause the at least one processor to train the second neural network.

14. The apparatus of claim 13, wherein the first training code is further configured to cause the at least one processor to train by generating a binary calcium segmentation mask from training data.

15. The apparatus of claim 13, wherein the second training code is further configured to cause the at least one processor to train the second neural network by annotating one or more training branches of a training data coronary artery and estimating ground truth density of the one or more branches.

16. The apparatus of claim 15, wherein the second training code is further configured to cause the at least one processor to train the second neural network by annotating four major branches of the training data coronary artery, and
wherein the four major branches comprise a left main artery, a left anterior descending artery, a left circumflex artery, and a right coronary artery.

17. The apparatus of claim 16, wherein the second training code is further configured to cause the at least one processor to train the second neural network by annotating other branches of the training data coronary artery in addition to the four major branches.

18. The apparatus of claim 13, wherein the first training data code is further configured to cause the at least one hardware processor to define a first loss in training the first neural network is differently than the second training code which is further configured to cause the at least one hardware processor to define a second loss in training the second neural network.

19. The apparatus of claim 11, wherein the assigning code is further configured to cause the at least one hardware processor to assign the coronary artery label by averaging a plurality of labels from a plurality of detected spots of calcium.

20. A non-transitory computer-readable medium storing instructions, the instructions comprising: one or more instructions that, when executed by one or more processors of a device, cause the one or more processors to:
receive image data;
generate a data indicating presence of calcium in one or more coronary arteries from the image data;
generate, in parallel with generating the data, a branch density of the one or more coronary arteries; and
assign a coronary artery label from the branch density to a specific one of the one or more coronary arteries.

* * * * *